United States Patent
Holenz et al.

(10) Patent No.: US 7,790,898 B2
(45) Date of Patent: Sep. 7, 2010

(54) SUBSTITUTED 3-PHENYLPIPERIDINE COMPOUNDS, THEIR PREPARATION AND USE

(75) Inventors: Joerg Holenz, Vilanova I la Geltru (ES); Helmut Buschmann, Esplugues de Llobregat (ES); Michael Finkam, Aachen (DE)

(73) Assignee: Gruenenthal GmbH, Aachen (DE)

( * ) Notice: Subject to any disclaimer, the term of this patent is extended or adjusted under 35 U.S.C. 154(b) by 52 days.

(21) Appl. No.: 11/698,195

(22) Filed: Jan. 26, 2007

(65) Prior Publication Data
US 2007/0173533 A1 Jul. 26, 2007

Related U.S. Application Data

(63) Continuation of application No. PCT/EP2005/008061, filed on Jul. 25, 2005.

(30) Foreign Application Priority Data

Jul. 27, 2004 (DE) .................. 10 2004 036 349

(51) Int. Cl.
C07D 211/42 (2006.01)
A61K 31/451 (2006.01)

(52) U.S. Cl. .................. 546/216; 546/202; 546/213; 546/214; 546/221; 514/324; 514/326; 514/327

(58) Field of Classification Search ............... 546/242, 546/202, 213, 216, 214, 221; 514/324, 326, 514/327
See application file for complete search history.

(56) References Cited

U.S. PATENT DOCUMENTS

| | | | | | |
|---|---|---|---|---|---|
| 3,438,991 | A | * | 4/1969 | Janssen | 546/217 |
| 3,575,990 | A | * | 4/1971 | Hermans | 546/217 |
| 4,072,685 | A | * | 2/1978 | Nedelec et al. | 546/238 |
| 4,147,872 | A | * | 4/1979 | Althuis et al. | 546/216 |
| 4,188,485 | A | * | 2/1980 | Kukla | 546/202 |
| 4,241,071 | A | * | 12/1980 | Martin et al. | 514/317 |
| 4,263,438 | A | * | 4/1981 | Althuis et al. | 546/216 |
| 4,382,942 | A | | 5/1983 | Nedelec et al. | |
| 4,460,594 | A | * | 7/1984 | Markwell | 514/323 |
| 4,593,037 | A | * | 6/1986 | Sarges | 514/317 |
| 4,623,728 | A | * | 11/1986 | Sarges | 546/236 |
| 4,962,115 | A | * | 10/1990 | Van Daele | 514/326 |
| 5,057,525 | A | * | 10/1991 | Van Daele | 514/318 |
| 5,137,896 | A | * | 8/1992 | Van Daele | 514/327 |
| 5,227,379 | A | * | 7/1993 | Jakobsen et al. | 514/228.2 |
| 6,124,323 | A | * | 9/2000 | Bigge et al. | 514/327 |
| 6,835,371 | B1 | * | 12/2004 | Elmaleh et al. | 424/9.1 |

| | | | | |
|---|---|---|---|---|
| 2004/0225003 | A1 | | 11/2004 | Sattlegger et al. |

FOREIGN PATENT DOCUMENTS

| | | | |
|---|---|---|---|
| DE | 31 49 703 | A1 | 6/1982 |
| EP | 372776 | A2 * | 6/1990 |
| WO | WO 00/39091 | A1 | 7/2000 |
| WO | WO 03/037863 | A2 | 5/2003 |

OTHER PUBLICATIONS

Hacksell et. al. "3-Phenylpiperidines. Central Dopamine-Autoreceptor Stimulating Activity" Journal of Medicinal Chemistry 1981, 24, 1475-1482.*
Sonesson et. al. "Substituted 3-Phenylpiperidines and Rigid Congeners as Preferential Dopamine Autoreceptor Antagonists: Synthesis and Structure-Activity Relationships" Journal of Medicinal Chemistry 1994, 37, 2735-2753.*
Wikstrom et. al. "Resolved 3-(3-Hydroxyphenyl)-N-n-propylpiperidine and Its Analogues: Central Dopamine Receptor Activity" Journal of Medicinal Chemistry 1984, 27, 1030-1036.*
Sui, Z. et. al. "An Efficient Synthesis of N-Aroyl-3-Phenyltetrahydropyridines" Synthetic Communications 1997, 27(1), 175-185.*
West, Anthony R., Solid State Chemistry and its Applications, Wiley, New York, 1988, pp. 358 & 365.*
Fused Ring and Bridged Fused Ring Nomenclature "http://www.chem.qmul.ac.uk/iupac/fusedring/FR1.html#14" online accessed Nov. 15, 2008.*
International Preliminary Report Form PCT/IB/373, PCT/15A/237 dated Jan. 2004 (Twenty (20) pages). Including English Translation.

* cited by examiner

*Primary Examiner*—Rita J Desai
*Assistant Examiner*—David K O'Dell
(74) *Attorney, Agent, or Firm*—Crowell & Moring LLP

(57) ABSTRACT

Substituted 3-phenylpiperidine compounds corresponding to Formula I

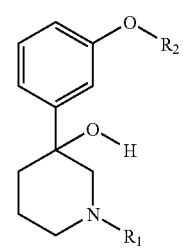

in which R1 and R2 have the meanings defined in the specification, methods for preparing such compounds, pharmaceutical compositions containing such compounds, and the use of such compounds for treating or inhibiting various conditions, especially pain.

19 Claims, No Drawings

SUBSTITUTED 3-PHENYLPIPERIDINE COMPOUNDS, THEIR PREPARATION AND USE

CROSS REFERENCE TO RELATED APPLICATIONS

This application is a continuation of international patent application no. PCT/EP2005/008061, filed Jul. 25, 2005, designating the United States of America, and published in German on Feb. 2, 2006 as WO 2006/010577, the entire disclosure of which is incorporated herein by reference. Priority is claimed based on Federal Republic of Germany patent application no. DE 10 2004 036 349.8, filed Jul. 27, 2004.

BACKGROUND OF THE INVENTION

The present invention relates to substituted 3-phenylpiperidine compounds, processes for their production, pharmaceutical compositions containing these compounds, as well as the use of these substances for the treatment or inhibition of various conditions, especially pain.

The treatment of chronic and non-chronic pain is of great importance in medicine. There is a universal need for highly effective pain therapies. The pressing need for a patient-friendly and target-oriented treatment of chronic and non-chronic pain, which is understood here to mean the successful and satisfactory treatment of pain for the patient, is documented in the large amount of scientific work that has recently appeared in the field of applied analgesics and in basic research on nociception.

Conventional opioids such as morphine are highly effective in the treatment of severe to extremely severe pain. Their use is restricted however on account of the known side effects, e.g. respiratory depression, vomiting, sedation, constipation and development of tolerance. Also, they are less effective in treating neuropathic or incidental pain, from which in particular patients with tumors suffer.

Among the opioids that are used in the treatment of pain, tramadol occupies a special position, since tramadol differs as regards its spectrum of side effects from conventional opioides (Analgesics—from Chemistry and Pharmacology to Clinical Application 228-230, Wiley 2002). Starting from tramadol it was now surprisingly found that the replacement of the cyclohexyldimethylamino group by a piperidine substituted on the nitrogen atom leads to substances effective in the treatment of pain.

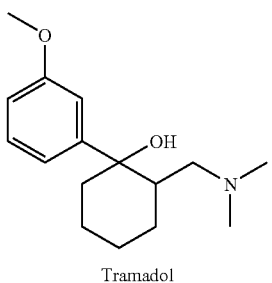

Tramadol

Of the class of substituted 3-phenylpiperidine compounds, up to now only one derivative is known from the literature. WO 0039091 discloses 3-(3-methoxyphenyl)-1-(phenylmethyl)-3-piperidinol as an intermediate product formed in the synthesis of bisarylpiperidines. In this compound the piperidine nitrogen is provided with a benzyl protective group, though functionalisations of the benzyl group are not described. Also, U.S. Pat. No. 4,382,942 (=DE 3149703) mentions 3-(3-methoxyphenyl)-1-(phenylmethyl)-3-piperidinol as an intermediate product.

SUMMARY OF THE INVENTION

An object of the present invention was to provide new compounds that are physiologically active with regard to analgesia.

Further objects of the invention were to provide compounds which are also suitable for use as anti-arrhythmia agents and/or antiemetics and/or nootropics (neurotropics) and/or for the treatment/therapy of cardiovascular conditions and/or urinary incontinence and/or diarrhea and/or pruritus and/or alcohol and/or drug and/or medicament dependency and/or inflammation and/or for the treatment of depression and/or for improving vigilance and/or for improving libido.

The present invention accordingly provides 3-phenylpiperidine compounds of formula I

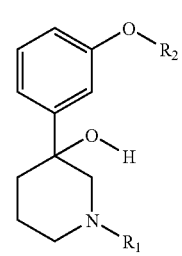

I wherein
$R^1$ denotes $C(O)R^3$ or $CH_2R^4$
$R^2$ denotes $C_{1-3}$ alkyl or H
$R^3$ denotes aryl, unsubstituted or singly or multiply substituted; thiophenyl, benzothiophenyl, benzofuranyl or furyl, unsubstituted or singly or multiply substituted; aryl, thiophenyl or furanyl bridged via a $(CHR^5)_n$-group or a $(CH_2)_nO$ group, and in each case unsubstituted or singly or multiply substituted, where n=1,2,3;
$R^4$ denotes singly or multiply substituted phenyl; naphthyl, fluoroanthenyl, fluorenyl, tetralinyl, indanyl or anthracenyl, unsubstituted or singly or multiply substituted; thiophenyl, benzothiophenyl, benzofuranyl or furyl, unsubstituted or singly or multiply substituted; aryl, thiophenyl or furyl bridged via a $(CHR^5)_n$ group or a $(CH_2)_nO$ group, and in each case unsubstituted or singly or multiply substituted, where n=1,2,3;
$R^5$ denotes H, $C_{1-3}$-alkyl, phenyl or benzyl, in each case unsubstituted or singly or multiply substituted, in the form of the racemate; in the form of the enantiomers, diastereomers, mixtures of the enantiomers or diastereomers or of an individual enantiomer or diastereomer; in the form of the bases and/or salts of physiologically compatible acids or cations.

Preferred in the context of this invention are substituted 3-phenylpiperidine compounds in which $R^3$ denotes aryl, unsubstituted or singly or multiply substituted; thiophenyl or furyl, unsubstituted or singly or multiply substituted; aryl bridged via a $CHR^5$ group or a $CH_2O$ group, unsubstituted or singly or multiply substituted.

Particularly preferred are substituted 3-phenylpiperidine compounds in which $R^3$ denotes phenyl or naphthyl, unsubstituted or singly or multiply substituted; unsubstituted thiophenyl or furyl; phenyl bridged via a $CHR^5$ group or a $CH_2O$ group, unsubstituted or singly or multiply substituted.

Also preferred are substituted 3-phenylpiperidine compounds in which $R^4$ denotes singly or multiply substituted phenyl, naphthyl, fluorenyl, indanyl or anthracenyl; thiophenyl or furyl, unsubstituted or singly or multiply substituted; aryl bridged via a $CHR^5$ group or a $CH_2O$ group, singly or multiply substituted.

Particularly preferred are substituted 3-phenylpiperidine compounds in which $R^4$ denotes singly or multiply substituted phenyl, naphthyl, unsubstituted thiophenyl or furyl; phenyl bridged via a $CHR^5$ group or a $CH_2O$ group, singly or multiply substituted.

Also preferred are 3-phenylpiperidine compounds in which $R^2$ denotes methyl or H.

Most particularly preferred are substituted 3-phenylpiperidine compounds selected from the group consisting of:
(2-fluorophenyl)-[3-hydroxy-3-(3-methoxyphenyl)-piperidine-1-yl]-methanone,
(3-fluorophenyl)-[3-hydroxy-3-(3-methoxyphenyl)-piperidine-1-yl]-methanone,
(4-fluorophenyl)-[3-hydroxy-3-(3-methoxyphenyl)-piperidine-1-yl]-methanone,
(2,3-difluorophenyl)-[3-hydroxy-3-(3-methoxyphenyl)-piperidine-1-yl]-methanone,
(2,5-difluorophenyl)-[3-hydroxy-3-(3-methoxyphenyl)-piperidine-1-yl]-methanone,
(3,5-difluorophenyl)-[3-hydroxy-3-(3-methoxyphenyl)-piperidine-1-yl]-methanone,
(3,4-dichlorophenyl)-[3-hydroxy-3-(3-methoxyphenyl)-piperidine-1-yl]-methanone,
[3-hydroxy-3-(3-methoxyphenyl)-piperidine-1-yl]-m-tolyl-methanone,
[3-hydroxy-3-(3-methoxyphenyl)-piperidine-1-yl]-p-tolyl-methanone,
[3-hydroxy-3-(3-methoxyphenyl)-piperidine-1-yl]-(3-trifluoromethylphenyl)-methanone,
[3-hydroxy-3-(3-methoxyphenyl)-piperidine-1-yl]-(4-methoxyphenyl)-methanone,
4-[3-hydroxy-3-(3-methoxyphenyl)-piperidine-1-carbonyl]-benzonitrile, furan-2-yl-[3-hydroxy-3-(3-methoxyphenyl)-piperidine-1-yl]-methanone,
[3-hydroxy-3-(3-methoxyphenyl)-piperidine-1-yl]-thiophen-2-yl-methanone,
1-[3-hydroxy-3-(3-methoxyphenyl)-piperidine-1-yl]-2-phenoxy-ethanone,
[3-hydroxy-3-(3-methoxyphenyl)-piperidine-1-yl]-(3,4,5-trimethoxyphenyl)-methanone,
[3-hydroxy-3-(3-methoxyphenyl)-piperidine-1-yl]-(4-nitrophenyl)-methanone,
(4-chloro-3-nitrophenyl)-[3-hydroxy-3-(3-methoxyphenyl)-piperidine-1-yl]-methanone,
(4-chlorophpenyl)-[3-hydroxy-3-(3-methoxyphenyl)-piperidine-1-yl]-methanone,
(2-bromophenyl)-[3-hydroxy-3-(3-methoxyphenyl)-piperidine-1-yl]-methanone,
(3-bromophenyl)-[3-hydroxy-3-(3-methoxyphenyl)-piperidine-1-yl]-methanone,
(4-bromophenyl)-[3-hydroxy-3-(3-methoxyphenyl)-piperidine-1-yl]-methanone,
(2,6-difluorophenyl)-[3-hydroxy-3-(3-methoxyphenyl)-piperidine-1-yl]-methanone,
(2,4-dichlorophenyl)-[3-hydroxy-3-(3-methoxyphenyl)-piperidine-1-yl]-methanone,
(3,5-bis-trifluoromethylphenyl)-[3-hydroxy-3-(3-methoxyphenyl)-piperidine-1-yl]-methanone,
acetic acid 2-[3-hydroxy-3-(3-methoxyphenyl)-piperidine-1-carbonyl]phenyl ester,
1-[3-hydroxy-3-(3-methoxyphenyl)-piperidine-1-yl]-2-phenyl-ethanone,
[3-hydroxy-3-(3-methoxyphenyl)-piperidine-1-yl]-naphthalene-2-yl-methanone,
1-[3-hydroxy-3-(3-methoxyphenyl)-piperidine-1-yl]-2,2-diphenyl-ethanone,
[3-hydroxy-3-(3-methoxyphenyl)-piperidine-1-yl]-(4-methyl-3-nitrophenyl)-methanone,
[3-hydroxy-3-(3-methoxyphenyl)-piperidine-1-yl]-(4-iodphenyl)-methanone,
1-(3-fluoro-benzyl)-3-(3-methoxyphenyl)-piperidine-3-ol hydrochloride,
1-(4-fluoro-benzyl)-3-(3-methoxyphenyl)-piperidine-3-ol hydrochloride,
1-(4-bromo-benzyl)-3-(3-methoxyphenyl)-piperidine-3-ol hydrochloride,
1-(2,6-difluoro-benzyl)-3-(3-methoxyphenyl)-piperidine-3-ol hydrochloride,
1-(3,5-difluoro-benzyl)-3-(3-methoxyphenyl)-piperidine-3-ol hydrochloride,
1-(3,4-dichloro-benzyl)-3-(3-methoxyphenyl)-piperidine-3-ol hydrochloride,
3-(3-methoxyphenyl)-1-(3-methyl-benzyl)-piperidine-3-ol hydrochloride,
3-(3-methoxyphenyl)-1-(4-methyl-benzyl)-piperidine-3-ol hydrochloride,
3-(3-methoxyphenyl)-1-(3-trifluoromethyl-benzyl)-piperidine-3-ol hydrochloride,
3-(3-methoxyphenyl)-1-(2-phenoxy-ethyl)-piperidine-3-ol hydrochloride,
3-(3-methoxyphenyl)-1-(4-nitro-benzyl)-piperidine-3-ol hydrochloride,
1-(4-methoxy-benzyl)-3-(3-methoxyphenyl)-piperidine-3-ol hydrochloride,
4-[3-hydroxy-3-(3-methoxyphenyl)-piperidine-1-ylmethyl]-benzonitrile hydrochloride,
1-furan-2-ylmethyl-3-(3-methoxyphenyl)-piperidine-3-ol hydrochloride,
3-(3-methoxyphenyl)-1-thiophen-2-ylmethyl-piperidine-3-ol hydrochloride,
3-(3-methoxyphenyl)-1-phenethyl-piperidine-3-ol hydrochloride,
1-(2,2-diphenyl-ethyl)-3-(3-methoxyphenyl)-piperidine-3-ol hydrochloride,
1-(3-bromo-benzyl)-3-(3-methoxyphenyl)-piperidine-3-ol hydrochloride,
3-(3-methoxyphenyl)-1-(4-methyl-3-nitro-benzyl)-piperidine-3-ol hydrochloride,
1-(4-chloro-3-nitro-benzyl)-3-(3-methoxyphenyl)-piperidine-3-ol hydrochloride,
1-(3,5-bis-trifluoromethyl-benzyl)-3-(3-methoxyphenyl)-piperidine-3-ol hydrochloride,
1-[3-hydroxy-3-(3-methoxyphenyl)-piperidine-1-yl]-3phenyl-propane-1-one,
(2-fluorophenyl)-[3-hydroxy-3-(3-hydroxyphenyl)-piperidine-1-yl]-methanone, and
(4-fluorophenyl)-[3-hydroxy-3-(3-hydroxyphenyl)-piperidine-1-yl]-methanone, in the form of the racemate; in the form of the enantiomers, diastereomers, mixtures of the enantiomers or diastereomers or of an individual enantiomer or diastereomer; in the form of the bases and/or salts of physiologically compatible acids or cations.

The compounds according to the invention have a marked affinity for the L-type Ca channel. They are therefore effective against pain (Analgesics—from chemistry and pharmacology to clinical application, pp. 353-378, Wiley 2002), intensify the effect of other analgesics (Methods Find. Expression. Clin. Pharmacol. 2000 Dec. 22, 741-745; Indian J. Exp. Biol. 2001 July;. 39, 636-642) and are furthermore also suitable for use as anti-arrhythmia agents and/or anti-emetics and/or nootropics (neurotropics) and/or for the treatment/therapy of cardiovascular conditions and/or urinary incontinence and/or diarrhea and/or pruritus and/or hypertension and/or alcohol and/or drug and/or medicament dependency and/or inflammation and/or for the treatment of depression and/or for improving vigilance and/or for improving libido.

The expression "$C_{1-3}$-alkyl" includes within the context of the present invention acyclic saturated or unsaturated hydrocarbon radicals, which may be branched or unbranched as well as unsubstituted or singly or multiply substituted, with 1, 2 or 3 C atoms, i.e. $C_{1-3}$-alkanyls, $C_{2-3}$-alkenyls and $C_{2-3}$-alkinyls. In this connection alkenyls contain at least one C=C double bond and alkinyls at least one C=C triple bond. In connection with the term "alkyl", the term "substituted" is understood within the meaning of the present invention to denote the substitution of one or more hydrogen atoms by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, $N(Alkyl)_2$, $N(alkylaryl)_2$, $N(alkyl$-heterorayl$)_2$, $N(cycloalkyl)_2$, $N(alkyl-OH)_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)$C_{1-16}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, =O, =S, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, $SO_2$-alkyl, $SO_2NH_2$, $SO_3H$, PO(O—$C_{1-6}$-alkyl)$_2$, Si($C_{1-6}$-alkyl)$_3$, Si($C_{3-8}$-cycloalkyl)$_3$, Si($CH_2$—$C_{3-8}$-cycloalkyl)$_3$, Si(phenyl)$_3$, cycloalkyl, aryl or heteroaryl, wherein multiply substituted radicals are understood to denote those radicals that are multiply, e.g. doubly or triply substituted, either on the same or on different atoms. Thus, it is possible according to the invention to have triple substitution on the same C atom, as in the case of —$CF_3$ or —$CH_2CF_3$, or at different positions, as in the case of —CH(OH)—CH=CH—$CHCl_2$. Multiple substitution may be carried out with the same or different substituents. If necessary a constituent may itself also be substituted; thus, —O alkyl includes, inter alia, also —O—$CH_2$—$CH_2$—O—$CH_2$—$CH_2$—OH. Substituents are preferably chosen from the group consisting of F, Cl, Br, I, —CN, $CF_3$, $NH_2$, OH, COOH, =O, $OCH_3$, $NO_2$, $COCH_3$, $COOCH_3$, $COOC_2H_5$ or N($CH_3$)$_2$. Advantageously alkyl is selected from the group consisting of methyl, ethyl, n-propyl, 2-propyl.

The expression "aryl" within the context of the present invention denotes carbocyclic ring systems with at least one aromatic ring, though without heteroatoms in only one of the rings, and includes inter alia phenyls, naphthyls and phenanthrenyls, fluoroanthenyls, fluoroenyls, indanyls and tetralinyls. The aryl radicals may also be condensed with further saturated, (partially) unsaturated or aromatic ring systems. Each aryl radical may be present unsubstituted or singly or multiply substituted, in which the aryl substituents may be identical or different and may be in any arbitrary and possible position of the aryl radical. Phenyl or naphthyl radicals are particularly advantageous.

The expression "heteroaryl" denotes a 5-, 6- or 7-membered cyclic aromatic radical that contains at least 1, possibly also 2, 3, 4, or 5 heteroatoms, in which the heteroatoms are identical or different and the heterocycle may be unsubstituted or singly or multiply substituted; in the case of substitution on the heterocycle the substituents may be identical or different and may be in any arbitrary and possible position of the heteroaryl radical. The heterocycle may also be part of a bicyclic or polycyclic system. Preferred heteroatoms are nitrogen, oxygen and sulfur. The heteroaryl radical is preferably selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, in which the bonding to the compounds of the general structure I may take place via any arbitrary and possible ring member of the heteroaryl radical.

With regard to "aryl" and "heteroaryl", the term "singly or multiply substituted" is understood within the context of the present invention to denote the single or multiple, e.g. double, triple, quadruple or five-fold, preferably single or double, substitution of one or more hydrogen atoms of the ring system by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, $N(Alkyl)_2$, $N(alkylaryl)_2$, $N(alkyl$-heterorayl$)_2$, $N(cycloalkyl)_2$, $N(alkyl-OH)_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=S)$C_{1-6}$-alkyl-aryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, C(=O)$NH_2$, C(=O)NH-alkyl, C(=O)NHaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, S(O)-alkyl, S(O)-aryl, $SO_2$-alkyl, $SO_2$-aryl, $SO_2NH_2$, $SO_3H$, $CF_3$, alkyl, cycloalkyl, aryl and/or heteroaryl, on one or possibly different atoms (in which connection a substituent may itself be substituted). The multiple substitution in this connection is preferably carried out with the same or with different substituents. Preferred are substituents selected from the group comprising F, Cl, Br, I, —CN, $NH_2$, OH, COOH, $OCF_3$, $CF_3$, $OCH_3$, $NO_2$, $OCOCH_3$, $COOCH_3$, $COOC_2H_5$ or N($CH_3$)$_2$.

The term "salt" is understood to denote any form of the active substance according to the invention in which it assumes an ionic form or is charged and is coupled to a counterion (a cation or anion) and/or is present in solution. This term also includes complexes of the active substance with other molecules and ions, in particular complexes that are complexed via ionic interactions. In particular the term is understood (and this is also a preferred embodiment of the present invention) to denote physiologically compatible salts, in particular physiologically compatible salts with cations or bases and physiologically compatible salts with anions or acids or also a salt formed with a physiologically compatible acid or a physiologically compatible cation.

The term "physiologically compatible salt with anions or acids" is understood within the context of the present invention to denote salts of at least one of the compounds according to the invention—generally protonated, preferably on the nitrogen atoms—as cation with at least one anion, which are physiologically compatible, in particular when used in humans and/or mammals. In particular the term is understood within the meaning of the present invention to denote the salt formed with a physiologically compatible acid, namely salts of the respective active substance with inorganic or organic acids, which are physiologically compatible, in particular when used in humans and/or mammals. Examples of physiologically compatible salts of specific acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharinic acid, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, phosphoric acid, maleic acid, malonic acid, hippuric acid and/or aspartic acid. The hydrochloride salt is particularly preferred.

The term "physiologically compatible salt with cations or bases" is understood within the context of the present invention to denote salts of at least one of the compounds according to the invention—generally a (deprotonated) acid—as anion with at least one, preferably inorganic, cation, which are physiologically compatible, in particular when used in humans and/or mammals. Particularly preferred are the salts of the alkali and alkaline earth metals, but also ammonium salts and in particular however (mono) or (di) sodium, (mono) or (di) potassium, magnesium or calcium salts.

The substances according to the invention are suitable as pharmaceutical active substances in medicaments. The invention therefore also provides medicaments or pharmaceutical compositions containing at least one substituted 3-phenylpiperidine compound according to the invention, as well as optionally suitable additives and/or auxiliary substances and/or optionally further active substances.

The pharmaceutical compositions according to the invention contain, in addition to at least one substituted 3-phenylpiperidine compound according to the invention, also possibly suitable additives and/or auxiliary substances, and thus also carrier materials, fillers, solvents, diluents, colorants and/or binders, and may be administered as liquid medicament forms in the form of injection solutions, droplets or ointments, as semi-solid medicament forms in the form of granules, tablets, pellets, patches, capsules, plasters or aerosols. The choice of the auxiliary substances, etc., as well as the amounts thereof to be used, depends on whether the pharmaceutical composition is to be administered orally, parenterally, intravenously, intraperitoneally, intradermally, intramuscularly, intranasally, buccaly, rectally, or topically, for example to the skin, the mucous membranes or the eyes. For oral administration suitable preparations are in the form of tablets, pills, capsules, granules, droplets, ointments and syrups, for parenteral, topical and inhalative administration suitable preparations are in the form of solutions, suspensions, easily reconstitutable dry preparations as well as sprays. 3-phenylpiperidine compounds according to the invention in depot form, in dissolved form or in a plaster, optionally with the addition of agents promoting penetration of the skin, are suitable percutaneous application preparations. Preparation forms that can be used orally or percutaneously can be formulated for the delayed release of the 3-phenylpiperidine compounds according to the invention. In principle further active substances known to persons skilled in the art may be added to the medicaments according to the invention.

The amount of active substance to be administered to the patient varies depending on the patient's weight, on the form of application, the medical condition and the severity of the condition. Normally 0.005 to 1000 mg/kg, preferably 0.05 to 5 mg/kg, of at least one 3-phenylpiperidine compound according to the invention is/are administered.

In a preferred form of the pharmaceutical composition a contained 3-phenylpiperidine compound according to the invention is present as pure enantiomer, as racemate, or as a non-equimolar or equimolar mixture of the enantiomers. In principle it is also possible, if a substituent contains one or more further stereocentres, to use pure diostereomers or a non-equimolar or equimolar mixture of the diostereomers.

The invention furthermore provides for the use of a 3-phenylpiperidine compound according to the invention for treating or inhibiting pain, in particular acute, neuropathic or chronic pain, and for the production of a medicament for use in such treatment.

The invention furthermore provides for the use of a 3-phenylpiperidine compound according to the invention in combination with a further analgesic, for example an opioid, for treating or inhibiting pain, in particular acute, neuropathic or chronic pain, and for the production of a medicament for use in such treatment.

It has surprisingly been found that the substituted 3-phenylpiperidine compounds of formula I are suitable for use as an anti-arrhythmia agent, antiemetic, nootropic (neurotropic), and/or for the treatment/therapy of cardiovascular conditions and/or urinary incontinence, diarrhea, pruritus, hypertension, alcohol and/or drug and/or medicament dependency, inflammation, for the treatment of depression, for improving vigilance and for improving libido.

The invention therefore also provides for the use of a substituted 3-phenylpiperidine compound of formula I as an anti-arrhythmia agent, antiemetic, nootropic (neurotropic), for the treatment or inhibition of cardiovascular conditions, urinary incontinence, diarrhea, pruritus, hypertension, alcohol and/or drug and/or medicament dependency, inflammation, for the treatment of depression, for improving vigilance and improving libido, and for the production of a medicament for use in such treatments.

Particularly preferably the substituted 3-phenylpiperidine compound according to the invention which are used for the production of a medicament for treating pain, in particular acute, neuropathic or chronic pain, depression, for treating cardiovascular conditions, urinary incontinence, diarrhea, pruritus, hypertension, alcohol and drug misuse, medicament dependency, inflammation for use as an anti-arrhythmia agent, antiemetic, nootropic, or for improving vigilance and for improving libido are selected from the following group:

(2-fluorophenyl)-[3-hydroxy-3-(3-methoxyphenyl)-piperidine-1-yl]-methanone, (3-fluorophenyl)-[3-hydroxy-3-(3-methoxyphenyl)-piperidine-1-yl]-methanone, (4-fluorophenyl)-[3-hydroxy-3-(3-methoxyphenyl)-piperidine-1-yl]-methanone, (2,3-difluorophenyl)-[3-hydroxy-3-(3-methoxyphenyl)-piperidine-1-yl]-methanone, (2,5-difluorophenyl)-[3-hydroxy-3-(3-methoxyphenyl)-piperidine-1-yl]-methanone, (3,5-difluorophenyl)-[3-hydroxy-3-(3-methoxyphenyl)-piperidine-1-yl]-methanone, (3,4-dichlorophenyl)-[3-hydroxy-3-(3-methoxyphenyl)-piperidine-1-yl]-methanone,
[3-hydroxy-3-(3-methoxyphenyl)-piperidine-1-yl]-m-tolyl-methanone,
[3-hydroxy-3-(3-methoxyphenyl)-piperidine-1-yl]-p-tolyl-methanone,
[3-hydroxy-3-(3-methoxyphenyl)-piperidine-1-yl]-(3-trifluoromethylphenyl)-methanone,
[3-hydroxy-3-(3-methoxyphenyl)-piperidine-1-yl]-(4-methoxyphenyl)-methanone,
4-[3-hydroxy-3-(3-methoxyphenyl)-piperidine-1-carbonyl]-benzonitrile, furan-2-yl-[3-hydroxy-3-(3-methoxyphenyl)-piperidine-1-yl]-methanone,
[3-hydroxy-3-(3-methoxyphenyl)-piperidine-1-yl]-thiophen-2-yl-methanone,
1-[3-hydroxy-3-(3-methoxyphenyl)-piperidine-1-yl]-2-phenoxy-ethanone,
[3-hydroxy-3-(3-methoxyphenyl)-piperidine-1-yl]-(3,4,5-trimethoxyphenyl)-methanone,
[3-hydroxy-3-(3-methoxyphenyl)-piperidine-1-yl]-(4-nitrophenyl)-methanone,
(4-chloro-3-nitrophenyl)-[3-hydroxy-3-(3-methoxyphenyl)-piperidine-1-yl]-methanone,
(4-chlorophpenyl)-[3-hydroxy-3-(3-methoxyphenyl)-piperidine-1-yl]-methanone,
(2-bromophenyl)-[3-hydroxy-3-(3-methoxyphenyl)-piperidine-1-yl]-methanone,
(3-bromophenyl)-[3-hydroxy-3-(3-methoxyphenyl)-piperidine-1-yl]-methanone,
(4-bromophenyl)-[3-hydroxy-3-(3-methoxyphenyl)-piperidine-1-yl]-methanone,
(2,6-difluorophenyl)-[3-hydroxy-3-(3-methoxyphenyl)-piperidine-1-yl]-methanone,
(2,4-dichlorophenyl)-[3-hydroxy-3-(3-methoxyphenyl)-piperidine-1-yl]-methanone,
(3,5-bis-trifluoromethylphenyl)-[3-hydroxy-3-(3-methoxyphenyl)-piperidine-1-yl]-methanone,
acetic acid 2-[3-hydroxy-3-(3-methoxyphenyl)-piperidine-1-carbonyl]phenyl ester,
1-[3-hydroxy-3-(3-methoxyphenyl)-piperidine-1-yl]-2phenyl-ethanone,
[3-hydroxy-3-(3-methoxyphenyl)-piperidine-1-yl]-naphthalene-2-yl-methanone,
1-[3-hydroxy-3-(3-methoxyphenyl)-piperidine-1-yl]-2,2-diphenyl-ethanone,
[3-hydroxy-3-(3-methoxyphenyl)-piperidine-1-yl]-(4-methyl-3-nitrophenyl)-methanone,
[3-hydroxy-3-(3-methoxyphenyl)-piperidine-1-yl]-(4-iodphenyl)-methanone,
1-(3-fluoro-benzyl)-3-(3-methoxyphenyl)-piperidine-3-ol hydrochloride,
1-(4-fluoro-benzyl)-3-(3-methoxyphenyl)-piperidine-3-ol hydrochloride,
1-(4-bromo-benzyl)-3-(3-methoxyphenyl)-piperidine-3-ol hydrochloride,
1-(2,6-difluoro-benzyl)-3-(3-methoxyphenyl)-piperidine-3-ol hydrochloride,
1-(3,5-difluoro-benzyl)-3-(3-methoxyphenyl)-piperidine-3-ol hydrochloride,
1-(3,4-dichloro-benzyl)-3-(3-methoxyphenyl)-piperidine-3-ol hydrochloride,
3-(3-methoxyphenyl)-1-(3-methyl-benzyl)-piperidine-3-ol hydrochloride,
3-(3-methoxyphenyl)-1-(4-methyl-benzyl)-piperidine-3-ol hydrochloride,
3-(3-methoxyphenyl)-1-(3-trifluoromethyl-benzyl)-piperidine-3-ol hydrochloride,
3-(3-methoxyphenyl)-1-(2-phenoxy-ethyl)-piperidine-3-ol hydrochloride,
3-(3-methoxyphenyl)-1-(4-nitro-benzyl)-piperidine-3-ol hydrochloride,
1-(4-methoxy-benzyl)-3-(3-methoxyphenyl)-piperidine-3-ol hydrochloride,
4-[3-hydroxy-3-(3-methoxyphenyl)-piperidine-1-ylmethyl]-benzonitrile hydrochloride,
1-furan-2-ylmethyl-3-(3-methoxyphenyl)-piperidine-3-ol hydrochloride,
3-(3-methoxyphenyl)-1-thiophen-2-ylmethyl-piperidine-3-ol hydrochloride,
3-(3-methoxyphenyl)-1-phenethyl-piperidine-3-ol hydrochloride,
1-(2,2-diphenyl-ethyl)-3-(3-methoxyphenyl)-piperidine-3-ol hydrochloride,
1-(3-bromo-benzyl)-3-(3-methoxyphenyl)-piperidine-3-ol hydrochloride,
3-(3-methoxyphenyl)-1-(4-methyl-3-nitro-benzyl)-piperidine-3-ol hydrochloride,
1-(4-chloro-3-nitro-benzyl)-3-(3-methoxyphenyl)-piperidine-3-ol hydrochloride,
1-(3,5-bis-trifluoromethyl-benzyl)-3-(3-methoxyphenyl)-piperidine-3-ol hydrochloride,
1-[3-hydroxy-3-(3-methoxyphenyl)-piperidine-1-yl]-3phenyl-propane-1-one,
(2-fluorophenyl)-[3-hydroxy-3-(3-hydroxyphenyl)-piperidine-1-yl]-methanone, and
(4-fluorophenyl)-[3-hydroxy-3-(3-hydroxyphenyl)-piperidine-1-yl]-methanone, in the form of the racemate; in the form of the enantiomers, diastereomers, mixtures of the enantiomers or diastereomers or of an individual enantiomer or diastereomer; in the form of the bases and/or salts of physiologically compatible acids or cations.

The present invention in addition provides a process for the production of the 3-phenylpiperidine compounds according to the invention as illustrated by the following reaction scheme. In order to produce the 3-phenylpiperidine compounds according to the invention, N-benzyl-piperidone is reacted with a 3-alkyloxyphenyl halide and a metal or an organometallic compound, for example magnesium or n-BuLi, in a suitable solvent, for example diethyl ether or THF, to form a 1-benzyl-3-(3-alkoxy-phenyl)-piperidine-3-ol compound. The benzyl group is removed by hydrogenation on a catalyst, for example Pd/C. By reaction with acid chlorides of formula $R^3(CO)Cl$ under the addition of a base, for example triethylamine, compounds according to the invention of formula Ia are obtained, which can be converted by reduction of the keto group, for example with lithium aluminium hydrides, in the presence of aluminium trichloride, into compounds of formula Ib.

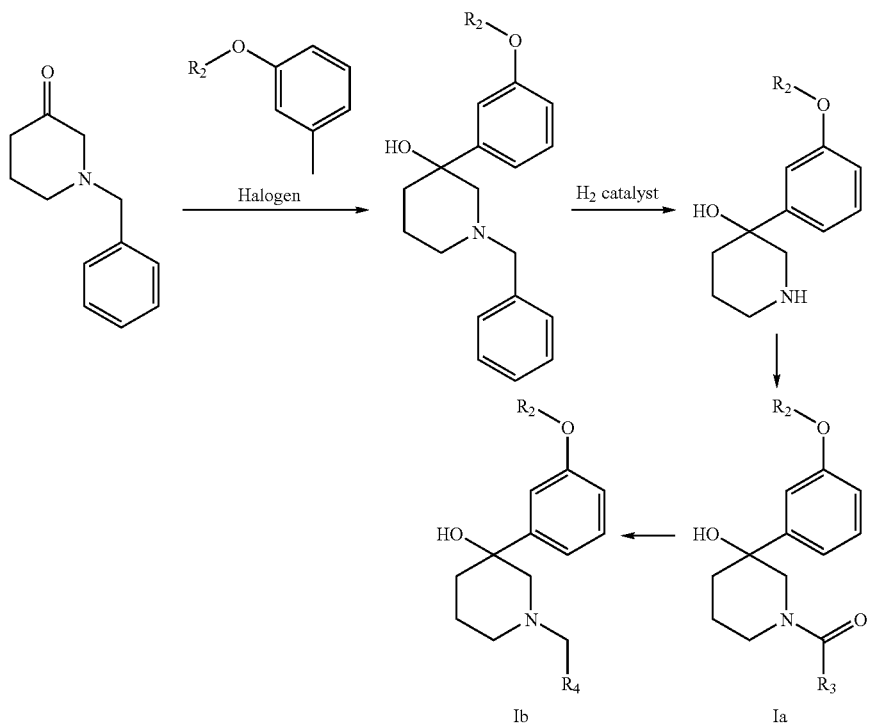

EXAMPLES

The following examples are intended to describe the invention in more detail without restricting its scope. The yields of the prepared compounds are not optimized. Silica gel 60 (0.040-0.063 mm) from E. Merck. Darmstadt, was used as stationary phase for the column chromatography. The thin-layer chromatography investigations were carried out with HPTLC precoated plates, silica gel 60 F 254, from E. Merck, Darmstadt. The mixture ratios of solvents for chromatographic investigations are always given in volume/volume.

1-Benzyl-3-(3-methoxy-phenyl)-piperidine-3-ol 4.22 g magnesium (Mg) in 50 mL THF and a speck of 12 were placed under a nitrogen atmosphere in a three-necked flask equipped with condenser, internal thermometer and dropping funnel. The mixture was heated to 50° C. while stirring and 22.1 ml of 3-bromoanisole in 50 ml THF were added dropwise within 30 minutes. The mixture was then stirred for a further 30 minutes at 70° C. After cooling with ice to 5° C., 22.34 g of N-benzyl-piperidone in 100 ml THF were added dropwise in 60 minutes. The mixture was stirred for a further 15 hours at room temperature. For the hydrolysis, 400 ml of 10% $NH_4HSO_4$ solution were added, acidified with dilute HCl, and then extracted with 100 ml of diethyl ether. The organic phase was extracted once with dilute HCl. The combined aqueous phases were made alkaline with NaOH and extracted three times with 100 ml portions of diethyl ether each time. The combined organic phases were concentrated by evaporation. Yield 35.05 g 3-(3-methoxy-phenyl)-piperidine-3-ol 32.41 g of 1-benzyl-3-(3-methoxy-phenyl)-piperidine-3-ol were dissolved in methanol and adjusted to pH 6 with 12.4 g of 32% HCl solution. 3.3 g Pd/C 10% (in cooled methanol) were added under a nitrogen atmosphere. The mixture was hydrogenated overnight at 5 bar $H_2$ pressure. The catalyst was then removed via a filter earth and the filtrate was concentrated by evaporation. The oily residue was taken up in $H_2O$, made alkaline with NaOH, and extracted three times with diethyl ether. The combined organic phases were dried over $MgSO_4$ and concentrated by evaporation. Yield 20.92 g 1-benzyl-3-[3-tetrahydropyrane-2-yloxy)-phenyl]-piperidine-3-ol 0.583 g magnesium (Mg) in 40 ml THF and a speck of 12 were placed under a nitrogen atmosphere in a three-necked flask equipped with condenser, internal thermometer and dropping funnel. The mixture was heated to 50° C. while stirring and 5.14 g of 2-(3-bromophenoxy)-tetrahydropyran in 50 ml THF were added dropwise while stirring. The mixture was then heated under reflux for a further 60 minutes. After cooling to 15° C., 4.83 g of N-benzyl-piperidone in THF were added dropwise. The mixture was stirred for a further 15 hours at room temperature. For the hydrolysis, 50 ml of saturated $NH_4HSO_4$ solution were added, the aqueous phase was extracted three times with ethyl acetate, and the organic phases were concentrated by evaporation. Yield 9.24 g 1-benzyl-3-(3-hydroxy-phenyl)-piperidine-3-ol 8.64 g of 1-benzyl-3-[3-(tetrahydropyrane-2-yloxy)-phenyl]-piperidine-3-ol were dissolved in 30 ml of ethanol and 8.9 ml of HCl were added. The solvent was removed after stirring the mixture for 60 hours. Yield 6 g 3-(3-hydroxy-phenyl)-piperidine-3-ol 2.7 g of 1-benzyl-3-3-hydroxy-phenyl)-piperidine-3-ol were dissolved in methanol. 2.5 g Pd/C 10% (in cooled methanol) were added under a nitrogen atmosphere. The mixture was hydrogenated overnight at 5 bar $H_2$ pressure. The catalyst was then removed via a filter earth and the filtrate was concentrated by evaporation. Yield 1.61 g General Preparation Protocol A:

To prepare the amides, 14.47 mmol of a corresponding acid chloride were dissolved in 10 ml of dichloromethane. After addition of 19.2 mmol of triethylamine and a spatula tip amount of DMAP (N,N-dimethylaminopyridine) 9.6 mmol of the amine in dichloromethane were added dropwise while cooling with ice. The reaction mixture was stirred for 15 hours at room temperature. 20 ml of $NH_4Cl$ were then added to the mixture, which was extracted three times with dichloromethane. After drying the mixture over $MgSO_4$ the solvent was removed and the product was purified by column chromatography (silica gel, n-hexane/ethyl acetate 1:10).

General Preparation Protocol B:

For the reduction of the keto group, 0.452 g of lithium aluminium hydride was placed in 50 ml of THF under a nitrogen atmosphere and 0.528 g of $AlCl_3$ was slowly added. After stirring for 45 minutes, 3.3 mmol of the corresponding amide in 50 ml of THF were added. The reaction mixture was refluxed for three hours, 50 ml of dilute NaOH were added, and the mixture was stirred for a further 15 hours. The mixture was extracted three times with diethyl ether; the organic phases were dried over $MgSO_4$, and the solvent was removed. To precipitate the HCl salt, the product was taken up in 25 ml of ether, and 0.386 ml of trimethylsilyl chloride was added. After stirring for 30 minutes in an ice bath the product was removed under suction.

Example 1

(2-fluorophenyl)-[3-hydroxy-3-(3-methoxyphenyl)-piperidine-1-yl]-methanone

The compound of Example 1 was prepared according to the general preparation protocol A from 2-fluorobenzoyl chloride and 3-(3-methoxy-phenyl)-piperidine-3-ol.

Example 2

(3-fluorophenyl)-[3-hydroxy-3-(3-methoxyphenyl)-piperidine-1-yl]-methanone

The compound of Example 2 was prepared according to the general preparation protocol A from 3-fluorobenzoyl chloride and 3-(3-methoxy-phenyl)-piperidine-3-ol.

Example 3

(4-fluorophenyl)-[3-hydroxy-3-(3-methoxyphenyl)-piperidine-1-yl]-methanone

The compound of Example 3 was prepared according to the general preparation protocol A from 4-fluorobenzoyl chloride and 3-(3-methoxy-phenyl)-piperidine-3-ol.

Example 4

(2,3-difluorophenyl)-[3-hydroxy-3-(3-methoxyphenyl)-piperidine-1-yl]-methanone

The compound of Example 4 was prepared according to the general preparation protocol A from 2,3-difluorobenzoyl chloride and 3-(3-methoxy-phenyl)-piperidine-3-ol.

Example 5

(2,5-difluorophenyl)-[3-hydroxy-3-(3-methoxyphenyl)-piperidine-1-yl]-methanone

The compound of Example 5 was prepared according to the general preparation protocol A from 2,5-difluorobenzoyl chloride and 3-(3-methoxy-phenyl)-piperidine-3-ol.

Example 6

(3,5-difluorophenyl)-[3-hydroxy-3-(3-methoxyphenyl)-piperidine-1-yl]-methanone

The compound of Example 6 was prepared according to the general preparation protocol A from 3,5-difluorobenzoyl chloride and 3-(3-methoxy-phenyl)-piperidine-3-ol.

Example 7

(3,4-dichlorophenyl)-[3-hydroxy-3-(3-methoxyphenyl)-piperidine-1-yl]-methanone

The compound of Example 7 was prepared according to the general preparation protocol A from 3,4-dichlorobenzoyl chloride and 3-(3-methoxy-phenyl)-piperidine-3-ol.

Example 8

[3-hydroxy-3-(3-methoxyphenyl)-piperidine-1-yl]-m-tolyl-methanone

The compound of Example 8 was prepared according to the general preparation protocol A from 3-methylbenzoyl chloride and 3-(3-methoxy-phenyl)-piperidine-3-ol.

Example 9

[3-hydroxy-3-(3-methoxyphenyl)-piperidine-1-yl]-p-tolyl-methanone

The compound of Example 9 was prepared according to the general preparation protocol A from 4-methylbenzoyl chloride and 3-(3-methoxy-phenyl)-piperidine-3-ol.

Example 10

[3-hydroxy-3-(3-methoxyphenyl)-piperidine-1-yl]-(3-trifluoromethylphenyl)-methanone The compound of Example 10 was prepared according to the general preparation protocol A from 3-trifluoromethylbenzoyl chloride and 3-(3-methoxy-phenyl)-piperidine-3-ol.

Example 11

[3-hydroxy-3-(3-methoxyphenyl)-piperidine-1-yl]-
(4-methoxyphenyl)-methanone

The compound of Example 11 was prepared according to the general preparation protocol A from 4-methylbenzoyl chloride and 3-(3-methoxy-phenyl)-piperidine-3-ol.

Example 12

4[3-hydroxy-3-(3-methoxyphenyl)-piperidine-1-
carbonyl]-benzonitrile

The compound of Example 12 was prepared according to the general preparation protocol A from 4-cyanobenzoyl chloride and 3-(3-methoxy-phenyl)-piperidine-3-ol.

Example 13

Furan-2-yl [3-hydroxy-3-(3-methoxyphenyl)-piperi-
dine-1-yl-methanone

The compound of Example 13 was prepared according to the general preparation protocol A from furan-2-carbonyl chloride and 3-(3-methoxy-phenyl)-piperidine-3-ol.

Example 14

[3-hydroxy-3-(3-methoxyphenyl)-piperidine-1-yl]-
thiophen-2-yl-methanone

The compound of Example 14 was prepared according to the general preparation protocol A from thiophene-2-carbonyl chloride and 3-(3-methoxy-phenyl)-piperidine-3-ol.

Example 15

1-[3-hydroxy-3-(3-methoxyphenyl)-piperidine-1-yl]-
2-phenoxy-ethanone

The compound of Example 15 was prepared according to the general preparation protocol A from phenoxyacetyl chloride and 3-(3-methoxy-phenyl)-piperidine-3-ol.

Example 16

[3-hydroxy-3-(3-methoxyphenyl)-piperidine-1-yl]-
(3,4,5-trimethoxyphenyl)-methanone The compound of Example 16 was prepared according to the general preparation protocol A from 3,4,5-trimethoxybenzoyl chloride and 3-(3-methoxy-phenyl)-piperidine-3-ol.

Example 17

[3-hydroxy-3-(3-methoxyphenyl)-piperidine-1-yl]-
(4-nitrophenyl)-methanone

The compound of Example 17 was prepared according to the general preparation protocol A from 4-nitrobenzoyl chloride and 3-(3-methoxy-phenyl)-piperidine-3-ol.

Example 18

(4-chloro-3-nitrophenyl)-[3-hydroxy-3-(3-methox-
yphenyl)-piperidine-1-yl]-methanone The compound of Example 18 was prepared according to the general preparation protocol A from 4-chloro-3-nitrobenzoyl chloride and 3-(3-methoxy-phenyl)-piperidine-3-ol.

Example 19

(4-chlorophenyl)-[3-hydroxy-3-(3-methoxyphenyl)-
piperidine-1-yl]-methanone

The compound of Example 19 was prepared according to the general preparation protocol A from 4-chlorobenzoyl chloride and 3-(3-methoxy-phenyl)-piperidine-3-ol.

Example 20

(2-bromophenyl)-[3-hydroxy-3-(3-methoxyphenyl)-
piperidine-1-yl]-methanone

The compound of Example 20 was prepared according to the general preparation protocol A from 2-bromobenzoyl chloride and 3-(3-methoxy-phenyl)-piperidine-3-ol.

Example 21

(3-bromophenyl)-[3-hydroxy-3-(3-methoxyphenyl)-
piperidine-1-yl]-methanone

The compound of Example 21 was prepared according to the general preparation protocol A from 3-bromobenzoyl chloride and 3-(3-methoxy-phenyl)-piperidine-3-ol.

Example 22

(4-bromophenyl)-[3-hydroxy-3-(3-methoxyphenyl)-
piperidine-1-yl]-methanone

The compound of Example 22 was prepared according to the general preparation protocol A from 4-bromobenzoyl chloride and 3-(3-methoxy-phenyl)-piperidine-3-ol.

Example 23

(2,6-difluorophenyl)-[3-hydroxy-3-(3-methoxyphe-
nyl)-piperidine-1-yl]-methanone The compound of Example 23 was prepared according to the general preparation protocol A from 2,6-diflourobenzoyl chloride and 3-(3-methoxy-phenyl)-piperidine-3-ol.

Example 24

(2,4-dichlorophenyl)-[3-hydroxy-3-(3-methoxyphe-
nyl)-piperidine-1-yl]-methanone The compound of Example 24 was prepared according to the general preparation protocol A from 2,4-dichlorobenzoyl chloride and 3-(3-methoxy-phenyl)-piperidine-3-ol.

Example 25

(3,5-bis-trifluoromethylphenyl)-[3-hydroxy-3-(3-methoxyphenyl)-piperidine-1-yl]methanone The compound of Example 25 was prepared according to the general preparation protocol A from 3,5-bis(trifluoromethyl)benzoyl chloride and 3-(3-methoxy-phenyl)-piperidine-3-ol.

Example 26

Acetic acid 2-[3-hydroxy-3-(3-methoxyphenyl)-piperidine-1-carbonyl]phenyl ester

The compound of Example 26 was prepared according to the general preparation protocol A from acetic acid 2-chlorocarbonyl phenyl ester and 3-(3-methoxy-phenyl)-piperidine-3-ol.

Example 27

1-[3-hydroxy-3-(3-methoxyphenyl)-piperidine-1-yl] 2phenyl ethanone

The compound of Example 27 was prepared according to the general preparation protocol A from phenylacetyl chloride and 3-(3-methoxy-phenyl)-piperidine-3-ol.

Example 28

[3-hydroxy-3-(3-methoxyphenyl)-piperidine-1-yl]-naphthalene-2-yl-methanone

The compound of Example 28 was prepared according to the general preparation protocol A from naphthalene-2-carbonyl chloride and 3-(3-methoxy-phenyl)-piperidine-3-ol.

Example 29

1-[3-hydroxy-3-(3-methoxyphenyl)-piperidine-1-y]2,2-diphenyl-ethanone

The compound of Example 29 was prepared according to the general preparation protocol A from diphenylacetyl chloride and 3-(3-methoxy-phenyl)-piperidine-3-ol.

Example 30

[3-hydroxy-3-(3-methoxyphenyl)-piperidine-1-yl]-(4-methyl-3-nitrophenyl)-methanone The compound of Example 30 was prepared according to the general preparation protocol A from 4-methyl-3-nitrobenzoyl chloride and 3-(3-methoxy-phenyl)-piperidine-3-ol.

Example 31

[3-hydroxy-3-(3-methoxyphenyl)-piperidine-1-yl]-(4-iodophenyl)-methanone

The compound of Example 31 was prepared according to the general preparation protocol A from 4-iodobenzoyl chloride and 3-(3-methoxy-phenyl)-piperidine-3-ol.

Example 32

1-(3-fluorobenzyl)-3-(3-methoxyphenyl)-piperidine-3-ol hydrochloride

The compound of Example 32 was prepared according to the general preparation protocol B of Example 2.

Example 33

1-(4-fluorobenzyl)-3-(3-methoxyphenyl)-piperidine-3-ol hydrochloride

The compound of Example 33 was prepared according to the general preparation protocol B of Example 3.

Example 34

1-(4-bromobenzyl)-3-(3-methoxyphenyl)-piperidine-3-ol hydrochloride

The compound of Example 34 was prepared according to the general preparation protocol B of Example 22.

Example 35

1-(2,6-difluorobenzyl)-3-(3-methoxyphenyl)-piperidine-3-ol hydrochloride

The compound of Example 35 was prepared according to the general preparation protocol B of Example 23.

Example 36

1-(3,5-difluorobenzyl)-3-(3-methoxyphenyl)-piperidine-3-ol hydrochloride

The compound of Example 36 was prepared according to the general preparation protocol B of Example 6.

Example 37

1-(3,4-dichlorbenzyl)-3-(3-methoxyphenyl)-piperidine-3-ol hydrochloride

The compound of Example 37 was prepared according to the general preparation protocol B of Example 7.

Example 38

3-(3-methoxyphenyl)-3-(3-methylbenzyl)-piperidine-3-ol hydrochloride

The compound of Example 38 was prepared according to the general preparation protocol B of Example 8.

Example 39

3-(3-methoxyphenyl)-1-(4-methylbenzyl)-piperidine-3-ol hydrochloride

The compound of Example 39 was prepared according to the general preparation protocol B of Example 9.

Example 40

3-(3-methoxyphenyl)-1-(3-trifluoromethylbenzyl)-piperidine-3-ol hydrochloride

The compound of Example 40 was prepared according to the general preparation protocol B of Example 10.

Example 41

3-(3-methoxyphenyl)-1-(2-phenoxy-ethyl)-piperidine-3-ol hydrochloride

The compound of Example 41 was prepared according to the general preparation protocol B of Example 15.

Example 42

3-(3-methoxyphenyl)-1-(4-nitrobenzyl)-piperidine-3-ol hydrochloride

The compound of Example 42 was prepared according to the general preparation protocol B of Example 17.

Example 43

1-(4-methoxybenzyl)-3-(3-methylphenyl)-piperidine-3-ol hydrochloride

The compound of Example 43 was prepared according to the general preparation protocol B of Example 11.

Example 44

4-[3-hydroxy-3-(3-methoxyphenyl)-piperidine-1-ylmethyl]-benzonitrile hydrochloride The compound of Example 44 was prepared according to the general preparation protocol B of Example 12.

Example 45

1-furan-2-ylmethyl-3-(3-methoxyphenyl)-piperidine-3-ol hydrochloride

The compound of Example 45 was prepared according to the general preparation protocol B of Example 13.

Example 46

3-(3-methoxyphenyl)-1-thiophen-2-ylmethyl-piperidine-3-ol hydrochloride

The compound of Example 46 was prepared according to the general preparation protocol B of Example 14.

Example 47

3-(3-methoxyphenyl)-1-phenethyl-piperidine-3-ol hydrochloride

The compound of Example 47 was prepared according to the general preparation protocol B of Example 27.

Example 48

1-(2,2-diphenyl-ethyl)-3-(3-methoxyphenyl)-piperidine-3-ol hydrochloride

The compound of Example 48 was prepared according to the general preparation protocol B of Example 29.

Example 49

1-(3-bromobenzyl)-3-(3-methoxyphenyl)-piperidine-3-ol hydrochloride

The compound of Example 49 was prepared according to the general preparation protocol B of Example 21.

Example 50

3-(3-methoxyphenyl)-1-(4-methyl-3-nitro-benzyl)-piperidine-3-ol hydrochloride

The compound of Example 50 was prepared according to the general preparation protocol B of Example 30.

Example 51

1-(4-chloro-3-nitro-benzyl)-3-(3-methoxyphenyl)-piperidine-3-ol hydrochloride

The compound of Example 51 was prepared according to the general preparation protocol B of Example 18.

Example 52

1-(3,5-bis-trifluoromethyl-benzyl)-3-(3-methoxyphenyl)-piperidine-3-ol hydrochloride The compound of Example 52 was prepared according to the general preparation protocol B of Example 25.

Example 53

1-[3-hydroxy-3-(3-methoxyphenyl)-piperidine-1-yl]-3phenyl-propane-1-one

The compound of Example 53 was prepared according to the general preparation protocol A from 3-phenyl-propionyl chloride and 3-(3-methoxy-phenyl)-piperidine-3-ol.

Example 54

(2-fluorophenyl)-[3-hydroxy-3-(3-hydroxyphenyl)-piperidine-1-yl]-methanone

The compound of Example 54 was prepared according to the general preparation protocol A from 3-fluorobenzoyl chloride and 3-(3-hydroxyphenyl)-piperidine-3-ol.

Example 55

(4-fluorophenyl)-[3-hydroxy-3-(3-hydroxyphenyl)-piperidine-1-yl]-methanone

The compound of Example 55 was prepared according to the general preparation protocol A from 4-fluorobenzoyl chloride and 3-(3-hydroxyphenyl)-piperidine-3-ol.

Biological Data: Investigations on Binding at the L-Calcium Channel Benzothiazepine Binding Site (Diltiazem Binding)

The biological membrane material was isolated from rat cerebral cortex. [$^3$H]-cis-(+)-diltiazem (5 nM in the batch) was used as ligand. Incubation was for 20 minutes at 25° C. The radioactivity measured in the presence of (±)-diltiazem ($10^{-6}$ M in the batch) is defined as the non-specific binding. The non-bound fraction of the radioactive ligand was separated after completion of the incubation, using a filtration process through Whatman glass fiber GF/B membranes. After being washed, the membranes were then measured in a β-counter. The method was developed based on the publication by Schoemaker and Langer (H. Schoemaker and S. Z. Langer (1985) Eur. J. Pharmacol. 111, 273-277). The $K_D$ value for this high affinity binding site was found to be 4.10±0.75 nM (N=3, i.e. mean values ±SEM from 3 independent series of experiments that had been carried out in the form of triple parallel experiments). Results for example compounds are shown in the following table:

| Example | Diltiazem binding [10 μM] % inhibition |
| --- | --- |
| 33 | 95 |
| 41 | 92.7 |
| 49 | 90.4 |
| 48 | 88.2 |
| 40 | 85.9 |
| 32 | 83.7 |
| 46 | 81.8 |
| 51 | 81.4 |
| 37 | 80.7 |
| 47 | 79.4 |
| 38 | 79.1 |
| 34 | 78.7 |
| 39 | 76 |
| 52 | 75.9 |
| 50 | 73.8 |
| 36 | 57.4 |
| 9 | 55.8 |
| 43 | 55 |
| 44 | 52.3 |
| 42 | 50 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted 3-phenylpiperidine compound corresponding to Formula I

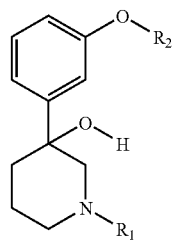

I wherein
$R^1$ denotes C(O)$R^3$ or CH$_2R^4$;
$R^2$ denotes $C_{1-3}$ alkyl or H;
$R^3$ denotes aryl, unsubstituted or singly or multiply substituted; thiophenyl, benzothiophenyl, benzofuranyl or furyl, unsubstituted or singly or multiply substituted; or aryl, thiophenyl or furanyl bridged via a (CHR$^5$)$_n$-group or a (CH$_2$)$_n$O group, and in each case unsubstituted or singly or multiply substituted, where n=1, 2 or 3;
$R^4$ denotes singly or multiply substituted phenyl; naphthyl, fluoroanthenyl, fluorenyl, tetralinyl, indanyl or anthracenyl, unsubstituted or singly or multiply substituted; thiophenyl, benzothiophenyl, benzofuranyl or furyl, unsubstituted or singly or multiply substituted; aryl, thiophenyl or furyl connected via a (CHR$^5$)$_n$ group or a (CH$_2$)$_n$O group, and in each case unsubstituted or singly or multiply substituted, where n=1, 2 or 3;
$R^5$ denotes H, $C_{1-3}$-alkyl, phenyl or benzyl, in each case unsubstituted or singly or multiply substituted,
in the form of a pure stereoisomer or a mixture of stereoisomers in any mixing ratio;
or a pharmaceutically acceptable salt thereof,
wherein
substituted $C_{1-3}$-alkyl is substituted with at least one member selected from the group consisting of F, Cl, Br, I, —CN, NH$_2$, NH-alkyl, NH-aryl, NH-cycloalkyl, NH-alkyl-OH, N(alkyl)$_2$, NO$_2$SH, S-alkyl, OH, O-alkyl, O-aryl, O-cycloalkyl, O-alkyl-OH, C(=O)C$_{1-6}$-alkyl, C(=O)aryl, C(=O)-cycloalkyl, CO$_2$H, CO$_2$-alkyl, C(=O)NH$_2$, =O, =S, C(=O)NH-alkyl, C(=O)N(alkyl)$_2$, SO$_2$NH$_2$, and SO$_3$H; and
a substituted aryl or substituted heteroaryl is substituted with at least one member selected from the group consisting of F, Cl, Br, I, CN, NH$_2$, NH-alkyl, NH-aryl, NH-alkyl-aryl, NH-cycloalkyl, NH-alkyl-OH, N(Alkyl)$_2$, N(alkylaryl)$_2$, N(cycloalkyl)$_2$, N(alkyl-OH)$_2$, NO$_2$, SH, S-alkyl, S-cycloalkyl, S-aryl, OH, O-alkyl, O-cycloalkyl, O-aryl, O-alkyl-aryl, O-alkyl-OH, C(=O)C$_{1-6}$-alkyl, C(=O)aryl, C(=S)aryl, C(=O)C$_{1-6}$-alkyl-aryl, C(=O)-cycloalkyl, CO$_2$H, CO$_2$-alkyl, CO$_2$-alkyl-aryl, C(=O)NH$_2$, C(=O)NH-alkyl, C(=O)NHaryl, C(=O)NH-cycloalkyl, C(=O)N(alky)$_2$, C(=O)N(alkyl-aryl)$_2$, C(=O)N(cycloalkyl)$_2$, SO$_2$NH$_2$, SO$_3$H, CF$_3$,alkyl, cycloalkyl, and aryl.

2. A compound according to claim 1, wherein said compound is in the form of a pure enantiomer, or a pharmaceutically acceptable salt thereof.

3. A compound according to claim 1, wherein said compound is in the form of a racemic mixture or a pharmaceutically acceptable salt thereof.

4. A compound according to claim 1, wherein $R^1$ denotes C(O)$R^3$.

5. A compound according to claim 1, wherein $R^1$ denotes CH$_2R^4$.

6. A compound according to claim 1, wherein $R^3$ denotes aryl, unsubstituted or singly or multiply substituted; thiophenyl, or furyl, unsubstituted or singly or multiply substituted; or aryl connected via a CHR$^5$ group or a CH$_2$O group, and unsubstituted or singly or multiply substituted.

7. A compound according to claim 1, wherein $R^3$ denotes phenyl or naphthyl, unsubstituted or singly or multiply substituted; unsubstituted thiophenyl or furyl; or phenyl connected via a CHR$^5$ group or a CH$_2$O group, and unsubstituted or singly or multiply substituted.

8. A compound according to claim 1, wherein $R^4$ denotes singly or multiply substituted phenyl, naphthyl, fluorenyl, indanyl or anthracenyl; thiophenyl or furyl, unsubstituted or singly or multiply substituted; or aryl connected via a $CHR^5$ group or a $CH_2O$ group, and singly or multiply substituted.

9. A compound according to claim 1, wherein $R^4$ denotes a singly or multiply substituted phenyl or naphthyl; unsubstituted thiophenyl or furyl; or phenyl connected via a $CHR^5$ group or a $CH_2O$ group, and singly or multiply substituted.

10. A compound according to claim 1, wherein $R^2$ denotes methyl or H.

11. A compound according to claim 1, selected from the group consisting of:
- (2-fluorophenyl)-[3-hydroxy-3-(3-methoxyphenyl)-piperidine-1-yl]-methanone,
- (3-fluorophenyl)-[3-hydroxy-3-(3-methoxyphenyl)-piperidine-1-yl]-methanone,
- (4-fluorophenyl)-[3-hydroxy-3-(3-methoxyphenyl)-piperidine-1-yl]-methanone,
- (2,3-difluorophenyl)-[3-hydroxy-3-(3-methoxyphenyl)-piperidine-1-yl]-methanone,
- (2,5-difluorophenyl)-[3-hydroxy-3-(3-methoxyphenyl)-piperidine-1-yl]-methanone,
- (3,5-difluorophenyl)-[3-hydroxy-3-(3-methoxyphenyl)-piperidine-1-yl]-methanone,
- (3,4-dichlorophenyl)-[3-hydroxy-3-(3-methoxyphenyl)-piperidine-1-yl]-methanone,
- [3-hydroxy-3-(3-methoxyphenyl)-piperidine-1-yl]-m-tolyl-methanone,
- [3-hydroxy-3-(3-methoxyphenyl)-piperidine-1-yl]-p-tolyl-methanone,
- [3-hydroxy-3-(3-methoxyphenyl)-piperidine-1-yl]-(3-trifluoromethylphenyl)-methanone,
- [3-hydroxy-3-(3-methoxyphenyl)-piperidine-1-yl]-(4-methoxyphenyl)-methanone,
- 4-[3-hydroxy-3-(3-methoxyphenyl)-piperidine-1-carbonyl]-benzonitrile,
- furan-2-yl-[3-hydroxy-3-(3-methoxyphenyl)-piperidine-1-yl]-methanone,
- [3-hydroxy-3-(3-methoxyphenyl)-piperidine-1-yl]-thiophen-2-yl-methanone,
- 1-[3-hydroxy-3-(3-methoxyphenyl)-piperidine-1-yl]-2-phenoxy-ethanone,
- [3-hydroxy-3-(3-methoxyphenyl)-piperidine-1-yl]-(3,4,5-trimethoxyphenyl)-methanone,
- [3-hydroxy-3-(3-methoxyphenyl)-piperidine-1-yl]-(4-nitrophenyl)-methanone,
- (4-chloro-3-nitrophenyl)-[3-hydroxy-3-(3-methoxyphenyl)-piperidine-1-yl]-methanone,
- (4-chlorophpenyl)-[3-hydroxy-3-(3-methoxyphenyl)-piperidine-1-yl]-methanone,
- (2-bromophenyl)-[3-hydroxy-3-(3-methoxyphenyl)-piperidine-1-yl]-methanone,
- (3-bromophenyl)-[3-hydroxy-3-(3-methoxyphenyl)-piperidine-1-yl]-methanone,
- (4-bromophenyl)-[3-hydroxy-3-(3-methoxyphenyl)-piperidine-1-yl]-methanone,
- (2,6-difluorophenyl)-[3-hydroxy-3-(3-methoxyphenyl)-piperidine-1-yl]-methanone,
- (2,4-dichlorophenyl)-[3-hydroxy-3-(3-methoxyphenyl)-piperidine-1-yl]-methanone,
- (3,5-bis-trifluoromethylphenyl)-[3-hydroxy-3-(3-methoxyphenyl)-piperidine-1-yl]-methanone,
- acetic acid 2-[3-hydroxy-3-(3-methoxyphenyl)-piperidine-1-carbonyl]phenyl ester,
- 1-[3-hydroxy-3-(3-methoxyphenyl)-piperidine-1-yl]-2-phenyl-ethanone,
- [3-hydroxy-3-(3-methoxyphenyl)-piperidine-1-yl]-naphthalene-2-yl-methanone,
- 1-[3-hydroxy-3-(3-methoxyphenyl)-piperidine-1-yl]-2,2-diphenyl-ethanone,
- [3-hydroxy-3-(3-methoxyphenyl)-piperidine-1-yl]-(4-methyl-3-nitrophenyl)-methanone,
- [3-hydroxy-3-(3-methoxyphenyl)-piperidine-1-yl]-(4-iodphenyl)-methanone,
- 1-(3-fluorobenzyl)-3-(3-methoxyphenyl)-piperidine-3-ol hydrochloride,
- 1-(4-fluoro-benzyl)-3-(3-methoxyphenyl)-piperidine-3-ol hydrochloride,
- 1-(4-bromo-benzyl)-3-(3-methoxyphenyl)-piperidine-3-ol hydrochloride,
- 1-(2,6-difluoro-benzyl)-3-(3-methoxyphenyl)-piperidine-3-ol hydrochloride,
- 1-(3,5-difluoro-benzyl)-3-(3-methoxyphenyl)-piperidine-3-ol hydrochloride,
- 1-(3,4-dichloro-benzyl)-3-(3-methoxyphenyl)-piperidine-3-ol hydrochloride,
- 3-(3-methoxyphenyl)-1-(3-methyl-benzyl)-piperidine-3-ol hydrochloride,
- 3-(3-methoxyphenyl)-1-(4-methyl-benzyl)-piperidine-3-ol hydrochloride,
- 3-(3-methoxyphenyl)-1-(3-trifluoromethyl-benzyl)-piperidine-3-ol hydrochloride,
- 3-(3-methoxyphenyl)-1-(2-phenoxy-ethyl)-piperidine-3-ol hydrochloride,
- 3-(3-methoxyphenyl)-1-(4-nitro-benzyl)-piperidine-3-ol hydrochloride,
- 1-(4-methoxy-benzyl)-3-(3-methoxyphenyl)-piperidine-3-ol hydrochloride,
- 4-[3-hydroxy-3-(3-methoxyphenyl)-piperidine-1-ylmethyl]-benzonitrile hydrochloride,
- 1-furan-2-ylmethyl-3-(3-methoxyphenyl)-piperidine-3-ol hydrochloride,
- 3-(3-methoxyphenyl)-1-thiophen-2-ylmethyl-piperidine-3-ol hydrochloride,
- 3-(3-methoxyphenyl)-1-phenethyl-piperidine-3-ol hydrochloride,
- 1-(2,2-diphenyl-ethyl)-3-(3-methoxyphenyl)-piperidine-3-ol hydrochloride,
- 1-(3-bromo-benzyl)-3-(3-methoxyphenyl)-piperidine-3-ol hydrochloride,
- 3-(3-methoxyphenyl)-1-(4-methyl-3-nitro-benzyl)-piperidine-3-ol hydrochloride,
- 1-(4-chloro-3-nitro-benzyl)-3-(3-methoxyphenyl)-piperidine-3-ol hydrochloride,
- 1-(3,5-bis-trifluoromethyl-benzyl)-3-(3-methoxyphenyl)-piperidine-3-ol hydrochloride,
- 1-[3-hydroxy-3-(3-methoxyphenyl)-piperidine-1-yl]-3-phenyl-propane-1-one,
- (2-fluorophenyl)-[3-hydroxy-3-(3-hydroxyphenyl)-piperidine-1-yl]-methanone, and
- (4-fluorophenyl)-[3-hydroxy-3-(3-hydroxyphenyl)-piperidine-1-yl]-methanone, in the form of a pure stereoisomer or a mixture of stereoisomers in any mixing ratio.

12. A process for preparing a compound according to claim 4, said process comprising reacting a 3-phenyl-piperidine-3-ol compound corresponding to Formula II

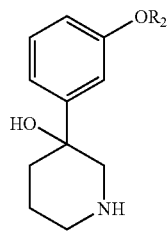

wherein $R^2$ denotes $C_{1-3}$ alkyl or H, with an acid chloride corresponding to the formula $R^3C(O)Cl$, wherein $R^3$ denotes aryl, unsubstituted or singly or multiply substituted; thiophenyl, benzothiophenyl, benzofuranyl or furyl, unsubstituted or singly or multiply substituted; or aryl, thiophenyl or furanyl bridged via a $(CHR^5)_n$-group or a $(CH_2)_nO$ group, and in each case unsubstituted or singly or multiply substituted, where n=1, 2 or 3.

13. A process for preparing a compound according to claim 5, said process comprising reducing the keto group of a compound corresponding to formula Ia

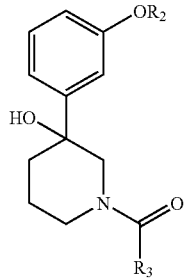

wherein
$R^2$ denotes $C_{1-3}$ alkyl or H; and
$R^3$ denotes aryl, unsubstituted or singly or multiply substituted; thiophenyl, benzothiophenyl, benzofuranyl or furyl, unsubstituted or singly or multiply substituted; or aryl, thiophenyl or furanyl connected via a $(CHR^5)_n$-group or a $(CH_2)_nO$ group, and in each case unsubstituted or singly or multiply substituted, where n=1, 2 or 3;
with a reducing agent.

14. A process according to claim 13, wherein the reducing agent is lithium aluminium hydride.

15. A pharmaceutical composition comprising a compound according to claim 1, and at least one pharmaceutical carrier or auxiliary agent.

16. A method of treating or inhibiting a condition selected from the group consisting of pain, and cardiac arrhythmia in a mammal, said method comprising administering an effective amount of a compound according to claim 1 to said mammal.

17. A method according to claim 16, for the treatment or inhibition of pain, wherein said pain is selected from the group consisting of acute pain, neuropathic pain, and chronic pain.

18. A method according to claim 16, wherein said compound is administered in combination with a further analgesic.

19. A method according to claim 18, wherein said further analgesic is an opioid.

* * * * *